United States Patent [19]

Khanna et al.

[11] Patent Number: 4,973,719
[45] Date of Patent: Nov. 27, 1990

[54] PROCESS FOR THE PRODUCTION OF ALPHA-6-DEOXYTETRACYCLINES

[75] Inventors: Jagmohan Khanna; Kiran Bala; Inder P. S. Grover, all of New Delhi, India

[73] Assignee: Ranbaxy Laboratories Limited, India

[21] Appl. No.: 263,728

[22] Filed: Oct. 28, 1988

[51] Int. Cl.$^5$ .......................................... C07C 237/48
[52] U.S. Cl. .................................................. 552/207
[58] Field of Search ............... 260/351.2, 351.5, 351.3; 556/23; 552/207

[56] References Cited

U.S. PATENT DOCUMENTS

| | | | |
|---|---|---|---|
| 3,200,149 | 8/1965 | Blackwood | 552/207 |
| 3,444,198 | 5/1969 | Korst | 552/207 |
| 3,549,780 | 12/1970 | Graneou | 174/21 |
| 3,639,439 | 2/1973 | Dewhurst | 551/23 |
| 3,907,890 | 9/1975 | Scanio | 552/207 |
| 3,954,862 | 5/1976 | Morris, Jr. | 552/207 |
| 3,962,131 | 6/1976 | Faubl et al. | 552/207 |
| 3,962,331 | 6/1976 | Cotti | 552/207 |
| 4,001,321 | 1/1977 | Faubl | 552/207 |
| 4,190,595 | 2/1980 | Diamond et al. | 556/23 |
| 4,207,258 | 6/1980 | Broggi et al. | 552/207 |
| 4,500,458 | 2/1985 | Villax et al. | 260/351.5 |
| 4,550,096 | 10/1985 | Page et al. | 552/207 |
| 4,743,699 | 5/1988 | Page et al. | 552/207 |

FOREIGN PATENT DOCUMENTS

| | | |
|---|---|---|
| 2216268 | 8/1974 | France . |
| 7401340 | 8/1974 | Netherlands ............... 260/351.5 |
| 1121642 | 7/1968 | United Kingdom . |
| 1121643 | 7/1968 | United Kingdom . |
| 1219768 | 1/1971 | United Kingdom . |
| 1138601 | 1/1989 | United Kingdom . |

OTHER PUBLICATIONS

Wilkinson et al., J. Chem. Soc., (1966), 1711–32.
Knowles et al., Chem. Communs. (1968), 1445.
Horner et al., Angew Chem. Int. Ed.; vol. 7, 942, (1968).
Vol. Pin et al., Russian Chem. Rev. 38, 273–289, (1969).
Ruesch et al., Tetrahedron, 25, 807–11, (1969).
Manfredi, Aspects of Homogenous Catalysis, vol. I, pp. 5–75, (1970).
Grubbs et al.; Journal of the American Society 93:12; 3062, (1971).
Kagan et al.; J. Am. Chem. Soc., 94, 6429 91 (1972).
Knowles et al., Chem. Comm., 10, (1972).
Harmon et al.; Chem. Rev. 73, 21–52, (1973).
Augustine et al., Am. N.Y. Sci., 158, 482–91, (1969).
Ruesch et al.; Tetrahedron, 25, 807–11, (1969).
Piers et al., Chem. Communs. 1069–70, (1969).
Manfredi, Aspects of Homogenous Catalysis, vol. I, pp. 5–75, (1970).
Manfredi, Homogenous Catalyst, Industrial Applications and Implications, vol. 70.
Grubbs et al., J. Am. Chem. Soc. 93, 3062, (1971).
Kagan et al., J. Am. Chem. Soc., 94, 6429, (1972).
Knowles et al., Chem. Communs. 10, (1972).
Harmon et al., Chem. Rev. 73, 21–52, (1973).
Robinson et al., J. Chem. Soc. 843–47, (1972).
J. Orgmetal Chem. 46, (1), 159–65, (1972).
J. Orgmetal Chem. 59, 161–166, (1973).
Chem. Ind. (London) 42, 1514, (1969).
Naturwissenschaften 56 (8), 415–16, (1969).
Inorg. Chem. 7(3), 546–51, (1968).
J. Org. Chem. 39, 1622, (1974).
Can. J. Chem. 52, 776, (1974).
J. Chem. Soc., Chem. Communs. (3), 114–15, (Eng), (1978).
Inorg. Chem. 17(11), 3069–74 (1978).
J. Mol. Catal. 7(4), 454–68, (Eng) (1980).
J. Organomet. Chem. 175, 222–232, (1979).
J. Organomet. Chem. 70, 89, (1974).
J. Organomet. Chem. Italy 912, 648, (1972).
Yakagaku 32 726 (1983).

*Primary Examiner*—Richard L. Raymond
*Assistant Examiner*—Raymond Covington
*Attorney, Agent, or Firm*—Bryan, Cave, McPheeters & McRoberts

[57] ABSTRACT

A process for the hydrogenation of a 6-methylenetetracycline in the production of alpha-6-deoxytetraclines, particularly the antibiotic doxycycline, in the presence of hydriodotetrakis (triphenylphosphine) rhodium (I) as a homogenous hydrogenation catalyst. The desired alpha-6-deoxy product is produced in high yields and stereospecificities, the process requiring the use of minimal quantities of rhodium metal in the hydrogenation catalyst per mole of the 6-methylenetetracycline hydrogenated.

12 Claims, No Drawings

PROCESS FOR THE PRODUCTION OF ALPHA-6-DEOXYTETRACYCLINES

This invention relates to a process for the preparation of alpha-6-deoxytetracyclines, and more particularly to such a process for the production of the antibiotic doxycycline, viz., alpha-6-deoxy-5-oxytetracycline.

BACKGROUND OF THE INVENTION

The preparation of doxycycline and other alpha-6-deoxytetracyclines was first described in Blackwood et al. U.S. Pat. No. 3,200,149 granted Aug. 10, 1965. That patent described their preparation by the catalytic hydrogenation of a corresponding 6-methylene intermediate, e.g., in the case of doxycycline, 11a-chloro-6-deoxy-6-demethyl-6-methylene-5-oxytetracycline (11a-chloro methacycline) or 6-deoxy-6-demethyl-6-methylene-5-oxytetracycline (methacycline), in the presence of a heterogeneous noble metal catalyst, e.g. palladium on carbon. The Blackwood patent disclosed the production, in yields of up to about 50%, of equimolar proportions of the diastereoisomers (epimers) of the 6-deoxytetracyclines. In the case of doxycycline, the patent disclosed the co-production of the corresponding beta epimer, beta-6-deoxy-5-oxytetracycline.

Subsequent efforts have been directed to the development of syntheses for producing the 6-deoxytetracyclines in greater yields and with greater stereoselectivity of formation of the desired alpha epimers, e.g., doxycycline. Thus, Korst U.S. Pat. No. 3,444,198 granted May 13, 1969, disclosed that the stereoselectivity of formation of the alpha epimers may be increased when the noble metal hydrogenation catalyst is poisoned. The Korst patent described the formation of epimeric mixtures of the 6-deoxytetracyclines in total yields of up to about 60%, with the stereoselective production of the alpha epimers in amounts of up to about 90% of the epimeric product mixtures. The use of other noble metal or noble metal salt compositions as heterogeneous hydrogenation catalysts in the production of doxycycline has also been disclosed in the literature. See, for example, Morris U.S. Pat. No. 3,954,862 granted May 4, 1976 and Faubl et al U.S. Pat. No. 3,962,131 granted June 8, 1976.

The use of rhodium halide complexes containing tertiary phosphine ligands, e.g., tris (triphenylphosphine) chloro rhodium (I), as homogeneous hydrogenation catalysts was first described by Wilkinson et al. in 1966. J. Chem. Soc. 1711-32. Subsequently, a number of soluble complexes of platinum metals, particularly rhodium, with halides and tertiary phosphines or the like, have been described as useful in a variety of regiospecific, stereoselective and asymmetric reduction reactions. See Knowles et al., Chem. Communs. 1445 (1968); Horner et al., Angew Chem. Int. Ed. 7, 942 (1968); Vol Pin et al., Russian Chemical Reviews, 38, 273-289 (1969); Augustine et al., Ann. N.Y. Sci., 158, 482-91 (1969); Ruesch et al., Tetrahedron, 25, 807-11 (1969); Piers et al., Chem. Communs. 1069-70 (1969); "Aspects Of Homogeneous Catalysis", Vol I, pp. 5-75 (1970), Carlo Manfredi, Milan, Italy; "Homogeneous Catalysis, Industrial Applications And Implications," Vol. 70, Advances in Chemistry Series, American Chemical Society; Grubbs et al., J. Am. Chem. Soc., 93, 3062 (1971); Kagan et al., J. Am. Chem. Soc., 94, 6429 (1972); Knowles et al., Chem. Communs. 10 (1972); and Harmon et al., Chem. Rev. 73, 21-52 (1973). Similar disclosures have been made in the patent literature. See, for example, U.S. Pat. Nos. 3,489,786; 3,549,780; and 3,639,439; and British Pat. Nos. 1,121,642; 1,121,643; 1,138,601; and 1,219,763.

The use of rhodium chloride/triphenylphosphine and similar complexes as homogeneous, stereospecific hydrogenation catalysts in the production of doxycycline and other alpha-6-deoxy-5-oxytetracyclines has also been extensively discussed in the patent literature. See, for example, U.S. Pat. Nos. 3,907,890; 3,962,331; 4,001,321; 4,207,258; 4,550,096; 4,743,699; and French Pat. No. 2,216,268.

The present invention is directed to an improved process for the production of doxycycline and other alpha-6-deoxytetracyclines, wherein the desired alpha epimer is produced in both high yield and stereospecificity, and the noble metal constituent of the hydrogenation catalyst is utilized in smaller proportions than heretofore required and is readily recoverable from the reaction mixture for re-use. Other objects and advantages of this invention will be apparent from the following description of preferred embodiments thereof.

SUMMARY OF THE INVENTION

This invention comprises an improved process for the preparation of alpha-6-deoxy-tetracyclines by the hydrogenation of the corresponding 6-methylenetetracyclines, in the presence of hydridotetrakis(triphenylphosphine) rhodium (I) in a homogeneous medium.

It has been found that when an appropriate 6-methylenetetracycline substrate is hydrogenated in the presence of such a homogeneous catalyst, the corresponding alpha-6-deoxytetracycline is produced in greater than about 95% yield and without the co-production of substantial amounts of the corresponding beta-6-deoxytetracycline epimer. Further, the hydrogenation may be carried out in the presence of substantially smaller quantities of rhodium than required in previously described homogeneous catalyses for the production of doxycycline or other alpha-6-deoxytetracyclines. Increased economies are thus achieved, both because of the decreased quantities of rhodium required for catalysis and because of the elimination of expensive purification operations heretofore required for separation of the undesired beta epimers.

PREFERRED EMBODIMENTS OF THE INVENTION

The process of this invention may be utilized in the production of any of the known alpha-6-deoxytetracyclines, preferably those having the formula:

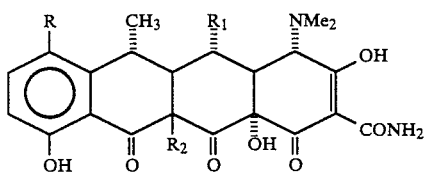

wherein
R and $R_2$ are each hydrogen or chloro, and $R_1$ is hydrogen or hydroxyl.

The preceding compounds are produced by hydrogenation of the corresponding 6-methylenetetracycline compounds of the formula:

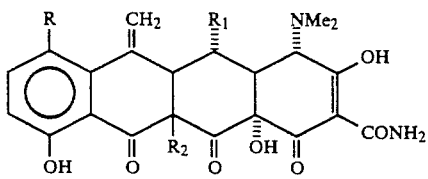

wherein R, R₁ and R₂ are as defined above.

6-methylenetetracyclines which are thus reacted may be prepared in the manner known in the art, e.g., as described in Blackwood U.S. Pat. No. 2,984,986 granted May 16, 1961 or Villax U.S. Pat. No. 3,848,491 granted Nov. 19, 1974.

Preferably, the catalytic hydrogenation is utilized to prepare doxycycline (wherein R is hydrogen and R₁ is hydroxyl) from 11a-chloro methacycline (wherein R is hydrogen, R₁ is hydroxyl, and R₂ is chloro).

The homogeneous catalyst used in the hydrogenation, hydridotetrakis(triphenylphosphine) rhodium (I) possesses excellent catalytic hydrogenation properties and greater stereospecificity than exhibited by previously proposed catalytic materials. It is produced by reacting a rhodium salt, preferably rhodium chloride; an alkali metal hydroxide, preferably potassium hydroxide; and a tertiary phosphine, preferably triphenylphosphine, at a temperature of about 78° C. for about 5 minutes in lower alcohols such as methanol, ethanol etc., essentially according to the method described by S. D. Robinson et al. in J.Chem. Soc. 843–47 (1972). Numerous other publications have described the preparation and applications of hydridotetrakis(triphenylphosphine) rhodium (I), e.g., J. Orgmetal. Chem. 46(1) 159–65 (1972); 59 161–66 (1973); Chem. Ind. (London) 42 1514 (1969); Naturwissenschaften 56(8) 415–16 (1969); Inorg. Chem. 7(3) 546–51 (1968); J. Organic Chem. 39, 1622 (1974); Can. J. Chem. 52, 776 (1974); J. Chem. Soc., Chem. Commun. (3), 114–15 (Eng.) (1978); Inorg. Chem. 17(11), 3069–74 (1978); J. Mol. Catal. 7(4), 454–68 (Eng.) (1980). The use of this material as a hydrogenation catalyst in the reduction of ketones to alcohol [J. Organomet. Chem. 175 222–232 (1979)], in the selective hydrogenation of dienes to mono-enes [J. Organomet. Chem. 70 89 (1974), Italy 912,648 (1972)], in the selective reduction of unsaturated esters and nitriles to corresponding saturated esters and nitriles, and in the hydrogenation of cyclohexene [U.S. 3,480,659 (1969), Yakagaku 32 726 (1983)] has also been described. It has not previously been described as useful in the hydrogenation of the 6-methylenetetracyclines.

The hydrogenation reaction is carried out in the manner known in the art, with the stereospecific formation of the desired alpha epimer in yields in excess of 95%. HPLC analyses of the hydrogenation products indicate beta-epimer contents of less than 0.5%. The hydrogenation is effected in the presence of from about 0.4 to 1.5 millimoles of catalyst per mole of 6-methylenetetracycline reacted. The amount of rhodium required for the reduction varies from about ¼ to 1/150th. of that required in previously described processes. Accordingly, the catalytic hydrogenation of the present invention provides superior yields and purities of the desired alpha-6-deoxytetracyclines, with substantially improved efficiencies in the operation.

The reaction is suitably carried out in a lower alkanolic solvent, preferably methanol, ethanol, propan-1-ol, propan-2-ol, or butanol. The solvents are degassed with nitrogen prior to use.

The reaction time depends on the amount of catalyst and the type of autoclave used for hydrogenation. Normally, to obtain high yields and purities, reaction times of from about 3 to 16 hours are utilized. It is preferred, but not critical, to carry out the reaction under pressures ranging from about 4 to 12 kg/cm², and at temperatures of from about 50° to 90° C. At temperatures lower than about 50° C. the reaction is too slow, and at higher temperatures decomposition occurs.

A small amount of triphenylphosphine, e.g., from about 30 to 60 millimoles per mole of the 6-methylenetetracycline substrate, when added to the reaction mixture prior to hydrogenation, acts as a promoter and accelerates the rate of hydrogen absorption, thus facilitating completion of the reaction. The optimum quantity of triphenylphosphine is determined empirically.

The doxycycline or other alpha-epimer is crystallized as an acid addition salt from the reaction mixture, preferably in the form of the sulfosalicylate salt (by adding excess sulfosalicylic acid). The purity is more than 99.5% by HPLC. The doxycycline sulfosalicylate is thereafter converted directly to doxycycline hyclate (the hemiethanolate hemihydrate) in stoichiometric yield by procedures known in the art.

The catalytic hydrogenation may be utilized in a single step to effect both the reductive dehalogenation and reduction of the 6-methylene group of an 11a-halo-6-deoxy-6-demethyl-6-methylenetetracycline, e.g., 11a-chloro methacycline. The corresponding alpha-6-deoxytetracycline, e.g., doxycycline, is directly produced in improved yield and purity, and with decreased rhodium consumption.

In a preferred embodiment, a mixture containing an 11a-halo-6-deoxy-6-demethyl-6-methylenetetracycline, preferably the p-toluene sulfonate of 11a-chloro methacycline; hydridotetrakis(triphenylphosphine) rhodium (I); and a tertiary phosphine, preferably triphenylphosphine, in methanol is subjected to agitation in a stainless steel autoclave, and hydrogenated at about 50° to 90° C. under a pressure between about 4 and 12 kg/cm², prior to the termination of the reaction. Sulfosalicylic acid is added and the reaction mixture is cooled to about 10° C. for 2–4 hours. The alpha-6-deoxy-5-oxytetracyline sulfosalicylate, preferably doxycyline sulfosalicylate (or toluene sulfonate) thus obtained is filtered and washed with methanol.

Alternatively, the reductive dehalogenation and hydrogenation can be carried out with a two-step process initially effecting 11a-dehalogenation with a conventional catalyst, e.g., 5% Rh/C or 5% Pd/C in methanol. The initial catalyst is then removed by filtration, and the solution is again subjected to hydrogenation in the presence of the above catalyst.

In the following examples, particularly preferred embodiments of the hydrogenation catalyst and the process for the preparation of alpha-6-deoxytetracyclines therewith are described. In the examples, all temperatures are given in Degrees Celsius and all parts and percentages by weight, unless otherwise specified.

EXAMPLE 1

Preparation of Hydridotetrakis(triphenylohosphine) Rhodium (I) Catalyst

Solutions of hydrated rhodium trichloride (0.26 g. 1.0 mM) in warm ethanol (20 ml), and potassium hydroxide (0.4 g., 7.1 mM) in warm ethanol (20 ml) were added in rapid succession to a vigorously stirred solution of triin corresponding examples of various prior art doxycycline synthesis patents in the following tabulation:

TABLE - I

Comparison of Doxycycline Produced in Example 2 With Prior Art Products

| Patent No. MOT | Example | Rhodium used per kg of MOT.HCl (mg) | Yield$^d$ (%) | Content (%) Alpha Isomer | Beta Isomer | MOT | Purity of isolated product (%) |
|---|---|---|---|---|---|---|---|
| US 4,207,258 | 2 | 19540 | 78.0 | NS | NS | NS | 99.3$^b$ |
| French 2,216,268 | 3 | 21252 | 90.6 | NS | NS | NS | NS |
| US 3,954,862 | 3 | 1962 | 80.0 | 81.0* | 1.6* | NS | NS$^a$ |
| US 4,001,321 | 1 | 9369 | 95.0 | 93.0 | 2.0–3.0* | NS | 93.0$^b$ |
| US 3,962,131 | 2 | less than 3332.4 | 98.8 | NS | NS | NS | 99.7$^b$ |
| US 3,907,890 | 5 | 0 | 75.2 | 98.0 | 2.0 | 0 | 98.0$^a$ |
| Re. 32,535 | 4 | 620.6 | 99.1 | 99.89 | 0 | 0 | 99.89$^c$ |
| Present Invention | 2 | 133.5 | 98.3 | 99.8 | 0.07 | None | 99.8$^a$ |

*Values in the reaction mixture
NS: Not stated
MOT: 6-deoxy-6-demethyl-6-methylene-5-oxytetracycline (methacycline).
$^a$HPLC analysis
$^b$UV analysis
$^c$Paper chromatography
$^d$Examples with highest yields considered for comparison purposes.
1200 G phenylphosphine (2.62 g. 10 mM) in boiling ethanol (80 ml). The mixture was heated under reflux for 5 minutes, cooled to 30° C., filtered and the solid washed with ethanol, water, ethanol and finally n-hexane. It was dried under vacuum to give a yellow microcrystalline solid (0.88 g., 77.4%); m. pt. 142°–47° C. (Found: C 75.3, H 5.2, Rh 8.7, Calc. C 75.0, H 5.35, Rh 8.9%).

EXAMPLE 2

Production of Doxycyline from Methacycline Hydrochloride with Hydridotetrakis (Triphenylohosphine) Rhodium (I) Catalyst Methacycline hydrochloride (20 g., 0.042 mole), 0.03 g of the catalyst prepared in Example 1 and methanol (240 ml) were charged to a stainless steel hydrogenation vessel. The reactants were hydrogenated at 80°–85° C. and at a pressure of 85–90 psi for 6 hours. Sulfosalicylic acid (32 g, 0.127 mole) was added to the reaction mixture, and the mixture was stirred for 3 hrs. at room temperature. Doxycycline sulfosalicylate (SSA) separated out immediately and was then filtered, washed first with water (100 ml), and then with methanol:water (1:1) (100 ml), and dried at 55°–60° C. The product weighed 27.2 g (98.3%). HPLC analysis indicated: alpha epimer 99.8%, beta epimer 0.07%, methacycline none, and others less than 0.1%.

The doxycycline SSA product was dissolved in hot 20% ethanolic-HCl (250 ml) and treated with activated charcoal (1.25 g) for 15 minutes. The reaction mixture was filtered through a G-4 sintered funnel. To the filtrate was added conc. hydrochloric acid (20 ml), and the mixture was agitated at 55°–60° C. for 3 hours. It was cooled to 40° C., filtered, washed with acetone (100 ml), and dried. The resulting doxycycline hyclate weighed 16.1 g (76.4%). A second crop was obtained as doxycycline SSA (3.6 g) by the addition of sulfosalicylic acid to the mother liquor.

The p-toluene sulfonate (PTS) salt of doxycycline was obtained when sulfosalicylic acid was replaced by p-toluene sulfonic acid.

The yield, stereospecificity, and purity of the product obtained in Example 2 are compared with those claimed From the preceding table it will be seen that the only prior art processes which resulted in the formation of doxycycline products in yields, stereospecificities, and purtities which even approached those obtained in Example 2 (the processes of U.S. Pat. Nos. 3,962,131 and Re. 32,535), required from five to as much as twenty-five times the amount of rhodium utilized in Example 2. Use of the procedure of Example 2 thus provides substantially and unexpectedly superior economies relative to each of the noted prior art procedures.

EXAMPLE 3

Example 2, when repeated with 0.040 g of the catalyst prepared as described in Example 1, yielded doxycycline SSA (26.8 g, 96.8%). The quality of the product was comparable to that obtained in Example 2.

EXAMPLE 4

Example 2 was repeated in the presence of triphenylphosphine (0.5 g). In this case the reaction was completed in 5 hrs. The yield of doxycycline SSA was 27.0 g (99.83%, beta epimer 0.05%, methacycline 0.05%, and other impurities less than 0.1%.

EXAMPLE 5

Production of Doxycycline from 11a-Chloro Methacycline PTS Salt with Hydridotetrakis (Triphenylphosphine) Rhodium (I) Catalyst 11a-chloromethacycline PTS salt (50 g, 0.076 mole), triphenylphosphine (23 g, 0.087 mole), and 0.055 g of the catalyst of Example 1 were mixed in methanol (300 ml) in a stainless steel pressure vessel. The reactor was thoroughly flushed with nitrogen. The reaction mixture was thereafter hydrogenated for 7 hrs at 80°–85° C. and under a pressure of 90–95 psi for 6.5 hrs. Doxycycline SSA was isolated in the manner described in Example 2 (47 g, 92.3%), and converted to its hyclate, yielding 28.2 g (77.52%) of product. No beta epimer or methacycline was detectable by thin layer chromatography. From the mother liquor, a second crop of doxycycline SSA was obtained, weighing 6.0 g. HPLC analysis:

alpha epimer 99.8%, beta epimer 0.19%, methacycline none and other less than 0.1%.

The yield, stereospecificity, and purity of the product obtained in Example 5 are compared with those claimed in corresponding examples of various prior art doxycycline synthesis patents in the following tabulation:

TABLE - II

Comparison of Doxycycline Produced in Example 5 With Prior Art Products

| U.S. Pat. No. | Example | Rhodium used per kg of 11a-Cl MOT (mg) | Yield$^d$ (%) | Content (%) alpha isomer | Content (%) beta isomer | MOT | Purity of isolated product (%)$^d$ |
|---|---|---|---|---|---|---|---|
| US 3,962,331 | 1 | 4889 | 70.1 | 95.0* | 5.0* | Slight traces | 98.9 |
| US 3,954,862 | 17 | 2140 | 86.7 | 59.9 | 1.33 | 0.8 | 59.0$^a$ |
| Re. 32,535 | 13 | 378.4 | 90.7 | 99.6 | 0.3 | 0 | 99.6$^a$ |
| Present Invention | 5 | 133.5 | 92.3 | 99.8 | 0.19 | NIL | 99.8$^a$ |

$^a$HPLC analysis; $^b$UV analysis; $^c$Paper chromatography; $^d$Examples with highest yields considered for comparison purposes.
MOT: 6-deoxy-6-demethyl-6-methylene-5-oxytetracycline (methacycline).
*In reaction mixture.
1200G From the preceding table it will be seen that the only prior art process which resulted in the formation of a doxycycline product in a yield, stereospecificity, and purity which even approached the values obtained in Example 5 (the process of reissue patent Re. 32,535), required almost three times more rhodium than employed in Example 5. Use of the procedure of Example 5 thus provides substantially and unexpectedly superior economies relative to the noted prior art process.

EXAMPLE 6

Example 5 was repeated except that doxycycline was isolated as its PTS salt (42.9 g, 90.6%). Thin layer chromatography of the product showed only traces of methacycline and beta epimer.

EXAMPLE 7

Example 5 was repeated using ethanol (300 ml) as the solvent instead of methanol. Thin layer chromatography showed principally doxycycline contaminated with only a negligible amount of methacycline and beta epimer.

EXAMPLE 8

Example 5 was repeated at 65°-70° C., maintaining the other conditions constant. In this case, the product yield was low (35 g, 68%). Thin layer chromatography of the product showed the presence of 3-4% methacycline.

EXAMPLE 9

Example 5 was repeated using 0.10 g of the Example 1 catalyst. The yield of doxycycline SSA was 46.5 g (91.39%). The purity of the product was comparable to that of the product obtained in Example 5.

EXAMPLE 10

11a-chloro methacycline PTS salt (40 g, 0.062 mole) and (50wet) 5% Rh/C (1.0 g) in methanol (240 ml) were charged to the hydrogenation vessel. The contents were hydrogenated at room temperature under a pressure of 0.5 kg/cm$^2$ until hydrogen absorption ceased (1 hour). Thin layer chromatography of the reaction mixture showed almost pure methacycline. The Rh/C catalyst was filtered off and the filtrate was charged back to the hydrogenator, followed by the addition of 0.07 g of the catalyst of Example 1 and triphenylphosphine (8.0 g, 0.03 mole). Hydrogenation was carried out under the conditions of temperature and pressure employed in Example 2. Doxycycline SSA (30.5 g, 74.9%) was obtained.

EXAMPLE 11

Preparation of Hydridotetrakis (Triphenyluphosphine) Rhodium (I) Catalyst, and Production of Doxycycline from 11a-Chloro Methacycline Therewith To a refluxing solution of triphenylphosphine (0.35 g, 1.34 mmol) in ethanol (15 ml) was added a hot solution of rhodium chloride (0.05g, 0.189 mmol) quickly followed by a hot solution of potassium hydroxide (0.077 g, 1.37 mmol). Almost immediately a yellow solid separated out. Refluxing was continued for 5 minutes. All operations were done under a nitrogen atmosphere.

The catalyst thus prepared was used without isolation, in the hydrogenation of 11a-chloro methacycline PTS (100 g, 0.154 mole). The reaction was carried out as described in Example 5, giving 92.2 g (90.6%) of doxycycline SSA after addition of sulfosalicylic acid. Thin layer chromatography showed a negligible amount of methacycline and no beta epimer.

It will be understood that various changes may be made in the procedures for preparing and utilizing the preferred catalyst embodiments described hereinabove without departing from the scope of the present invention. Accordingly, it is intended that the invention is not limited to the preceding description but should be construed in the light of the following claims:

We claim:

1. In a process for the preparation of an alpha-6-deoxytetracycline by the hydrogenation of a substrate selected from the group consisting of an 11a-chloro-6-deoxy-6-demethyl-6-methylenetetracycline, a 6-deoxy-6-demethyl-6-methylenetetracycline and salts thereof, the improvement comprising conducting the hydrogenation in the presence of from 0.4 to 1.5 millimols of a homogeneous hydrogenation catalyst comprising hydridotetrakis (triphenylphosphine) rhodium (I).

2. The process of claim 1, wherein the hydrogenation is carried out in the presence of from 0.4 to 1.5 millimoles of said catalyst and from 30 to 60 millimoles of a tertiary phosphine promoter, per mole of said substrate.

3. The process of claim 1, wherein the hydrogenation is carried out under pressures of from 4 to 12 kg/cm$^2$ and at temperatures of from 50° to 90° C., and the alpha- 6-deoxytetracycline is recovered in the form of the sulfosalicylate or p-toluene sulfonate salt thereof.

4. The process of claim 1, for producing doxycycline, wherein the substrate is 11a-chloro methacycline, methacycline, or an acid addition salt thereof.

5. The process of claim 4, wherein the hydrogenation is carried out in the presence of from 0.4 to 1.5 millimoles of said catalyst and from 30 to 60 millimoles of a tertiary phosphine promoter, per mole of said substrate.

6. The process of claim 4, wherein the hydrogenation is carried out under pressures of from 4 to 12 kg/cm² and at temperatures of from 50° to 90° C., and the doxycycline is recovered in the form of the sulfosalicylate or p-toluenesulfonate salt thereof.

7. A method of producing doxycycline which comprises doxycycline which comprises hydrogenating 11-a-chloromethacycline p-toluenesulfonate salt in the presence of an effective amount of triphenylphosphine promoter and 0.4–1.5 millimoles of hydridotetrakis (triphenylphosphine) rhodium I catalyst per mole of chloromethacycline under pressure of 90 to 95 psi for a time and at a temperature sufficient to produce a high yield of doxycycline containing less than 0.5% of the beta-isomer.

8. A method of producing doxycycline which comprises hydrogenating 6-methacycline hydrochloride in the presence of from 0.4 to 1.5 millimoles of hydridotetrakis rhodium I catalyst per mol of methacycline in a lower alkanol solvent at a temperature from 80°–85° C. at a pressure of 85–90 psi for a time sufficient to produce a high yield of doxycycline containing less than 0.5% of the beta-isomer.

9. A process for preparing an α-6-deoxytetracycline by hydrogenation of a 6-methylenetetracycline having the formula

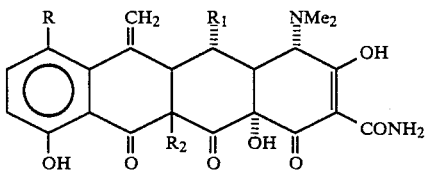

wherein R and R₂ are H or Cl and R₁ is H or OH, in the presence of from 0.4–1.5 millimoles of hydridotetrakis rhodium I catalyst in the presence of a lower alkanol solvent at a temperature so as to produce a high yield of an α-6-deoxytetracycline having a beta-isomer content of less than 0.5%.

10. A process according to claim 9 wherein R is H, R₁ is OH and R₂ is Cl.

11. A process according to claim 10 wherein, after hydrogenation is complete, an excess of sulfosalicylic acid is added and th'reaction mixture is cooled to about 10° C. to precipitate α-6-deoxy-5-oxytetracycline sulfosalicylate.

12. A process for preparing doxycycline which comprises dehalogenating 11-a-halo-6-deoxy-6-demethyl-6-methylene tetracycline in the presence of a catalyst selected from the group consisting of rhodium on carbon and palladium on carbon in a lower alkanol solvent, filtering to remove the catalyst and hydrogenating the product in the presence of from 0.4–1.5 millimoles of hydridotetrakis rhodium I catalyst at a temperature so as to produce a high yield of doxycycline having a beta-isomer content of less than 0.5%.

* * * * *

UNITED STATES PATENT AND TRADEMARK OFFICE
CERTIFICATE OF CORRECTION

PATENT NO. : 4,973,719

DATED : November 27, 1990

INVENTOR(S) : JAGMOHAN KHANNA et al.

It is certified that error appears in the above-identified patent and that said Letters Patent is hereby corrected as shown below:

Column 5, lines 37-38, change "(Triphenylohosphine)" to --(Triphenylphosphine)--

Column 6, lines 48-50 change "27.0 g (99.83%, beta epimer 0.05%, methacycline 0.05%, and other impurities less than 0.1%." to --27.0 g (97.6%). HPLC analysis of the product indicated alpha epimer 99.83%, beta epimer 0.05%, methacycline 0.05%, and other impurities less than 0.1%.--

Column 7, line 62 change "(50 wet)" to --(50% wet)--

Column 8, line 28 change "(Triphenyluphosphine)" to --(Triphenylphosphine)--

Column 9, lines 17-18 in Amendment dated July 16, 1990 delete "which comprises doxycycline"

Column 9, lines 30-31 in Amendment dated July 16, 1990 change "hydridotetrakis rhodium" to --hydridotetrakis (triphenylphosphine) rhodium--

UNITED STATES PATENT AND TRADEMARK OFFICE
CERTIFICATE OF CORRECTION

PATENT NO. : 4,973,719

DATED : November 27, 1990

INVENTOR(S) : JAGMOHAN KHANNA et al.

It is certified that error appears in the above-identified patent and that said Letters Patent is hereby corrected as shown below:

Column 10, line 23 in Amendment dated July 16, 1990 change "tn'" to --the--

Column 10, line 33 in Amendment dated July 16, 1990 Change "hydridotetrakis rhodium" to --hydridotetrakis (triphenylphosphine) rhodium--

Signed and Sealed this

First Day of September, 1992

Attest:

DOUGLAS B. COMER

Attesting Officer

Acting Commissioner of Patents and Trademarks